(12) United States Patent
Zborowski et al.

(10) Patent No.: US 6,412,359 B1
(45) Date of Patent: Jul. 2, 2002

(54) SYSTEM AND DEVICE FOR DETERMINING PARTICLE CHARACTERISTICS

(75) Inventors: Maciej Zborowski, Bay Village; Jeff Chalmers, Columbus; Lee Robert Moore, Cleveland Heights, all of OH (US)

(73) Assignees: The Cleveland Clinc Foundation, Cleveland; The Ohio State University, Columbus, both of OH (US)

( * ) Notice: Subject to any disclaimer, the term of this patent is extended or adjusted under 35 U.S.C. 154(b) by 0 days.

(21) Appl. No.: 09/607,702

(22) Filed: Jun. 30, 2000

Related U.S. Application Data

(62) Division of application No. 09/020,327, filed on Feb. 6, 1998, now Pat. No. 6,082,205.

(51) Int. Cl.[7] .............................................. G01N 21/00
(52) U.S. Cl. ...................................................... 73/865.5
(58) Field of Search ........................... 73/865.5, 61.69; 324/71.4, 201, 228; 348/142

(56) References Cited

U.S. PATENT DOCUMENTS 4,102,780 A * 7/1978 Sun et al.

OTHER PUBLICATIONS

"Single Cell Magnetophoresis and its Diagnostic Value." Journal of Magnetism and Magnetic Materials 122, pp. 367–370, 1993.
"Magnetocytometer for Biological Applications." Christian–Albrechts–University of Kiel, (3 pages), no date.
"Analytical Cell Magnetophoresis." V. Chikov, A. Kuznetsov and W. Schütt, Institute for Chemical Physics Moscow and Department of Internal Medicine, University Rostock, pp. 381–389, no date.
"Magnetophoresis: I. Detection of Magnetically Labeled Cells." S. Winoto–Morbach, V. Tchikov, and W. Müller–Ruchholtz, Journal of Clinical Laboratory Analysis 8:400–406, 1994.

(List continued on next page.)

*Primary Examiner*—Robert Raevis
(74) *Attorney, Agent, or Firm*—Nenad Pejic; Calfee, Halter & Griswold LLP

(57) ABSTRACT

The present invention provides methods and apparatuses for determining at least one of a plurality of particle physical characteristics. The particle physical characteristics include particle size, shape, magnetic susceptibility, magnetic label density, charge separation, dielectric constant, and derivatives thereof. The method includes generating a region of space having a substantially constant force field, determining the velocity of at least one particle within the region by identifying and locating the particle and its coordinates in at least two temporally defined digital images, and determining the particle physical characteristics from the determined velocity and a predetermined force field magnitude and direction. A device for determining one or more particle physical characteristics is described which has a force field device for subjecting at least one particle to at least one force field, a substantially transparent flow channel, and a computer system for gathering and analyzing data associated with the at least one particle. A system for determining one or more particle physical characteristics is provided which has a force field device for generating at least one force field having a predetermined force field magnitude and direction and for subjecting at least one particle to the at least one force field, a flow system for regulating the introduction of the at least one particle into the force field device, and a computer system for gathering and analyzing data associated with the at least one particle. A pole piece assembly for producing a region of space having a substantially constant magnetic force field is also provided.

12 Claims, 6 Drawing Sheets

OTHER PUBLICATIONS

"Magnetophoresis: II. Quantification of Iron and Hemoglobin Content at the Single Erythrocyte Level." S. Winoto–Morbach, V. Tchikov, and W. Müller–Ruchholtz, Journal of Clinical Laboratory Analysis 9:42–46, 1995.

"Magnetocytometry for Detecting Cell Labeling with Magnetic Immunomicrospheres." V. Tchikov, S. Winoto–Morbach, and W. Müller–Ruchholtz, pp. 176–185, no date.

"Biomedical and Clinical Applications of Automated Single Cell Electrophoresis." VCH Verlagsgesellscnatt mbH, D–6940 Weinheim, (6 pages), 1990.

"Electrophoretic Fingerprinting and the Biological Activity of Colloidal Indicators." B.J. Marlow, D. Fairhurst and W. Schutt, LANGMUR, (5 pages), 1988.

"Cell Electrophoresis: Proceedings of the International Meeting, Rostock, German Democratic Republic, Sep. 24–28, 1984." Walter de Gruyter, pp. 87–93, 1985.

"Determination of the Magnetic Susceptibility of Labeled Particles by Video Imaging." Chemical Engineering Science, vol. 51, No. 6, pp. 947–956, 1996.

"Quantitative Analysis of Leukocyte Membrane Antigen Expression: Normal Adult Values." Cytometry (Communications in Clinical Cytometry) 26:137–147, 1996.

"Application of Magnetic Susceptibility Gradients to Magnetic Separation." American Institute of Physics, vol. 55, No. 6, pp. 2592–2594, 1984.

"Observation of Particle Trajectories Near a Magnetized Fiber." United States Department of Energy, Morgantown Energy Technology Center, pp. 1–35, 1978.

"Magnetophoretic Techniques." Moscow, Rostock, (3 pages), 1985.

* cited by examiner

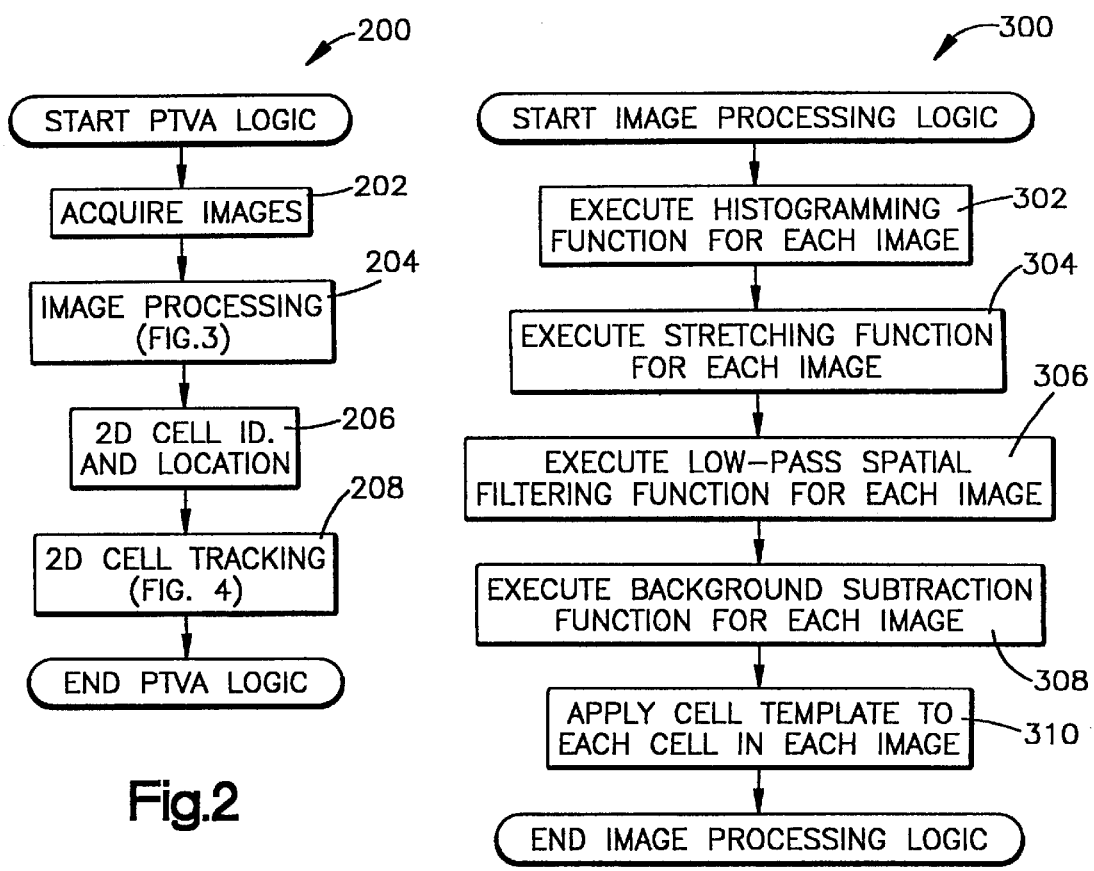
Fig.2
Fig.3
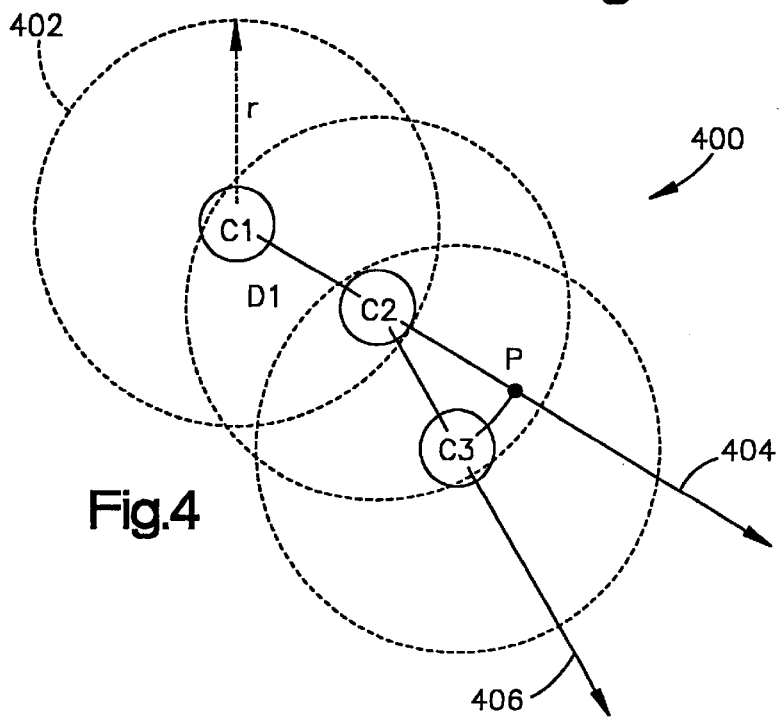
Fig.4

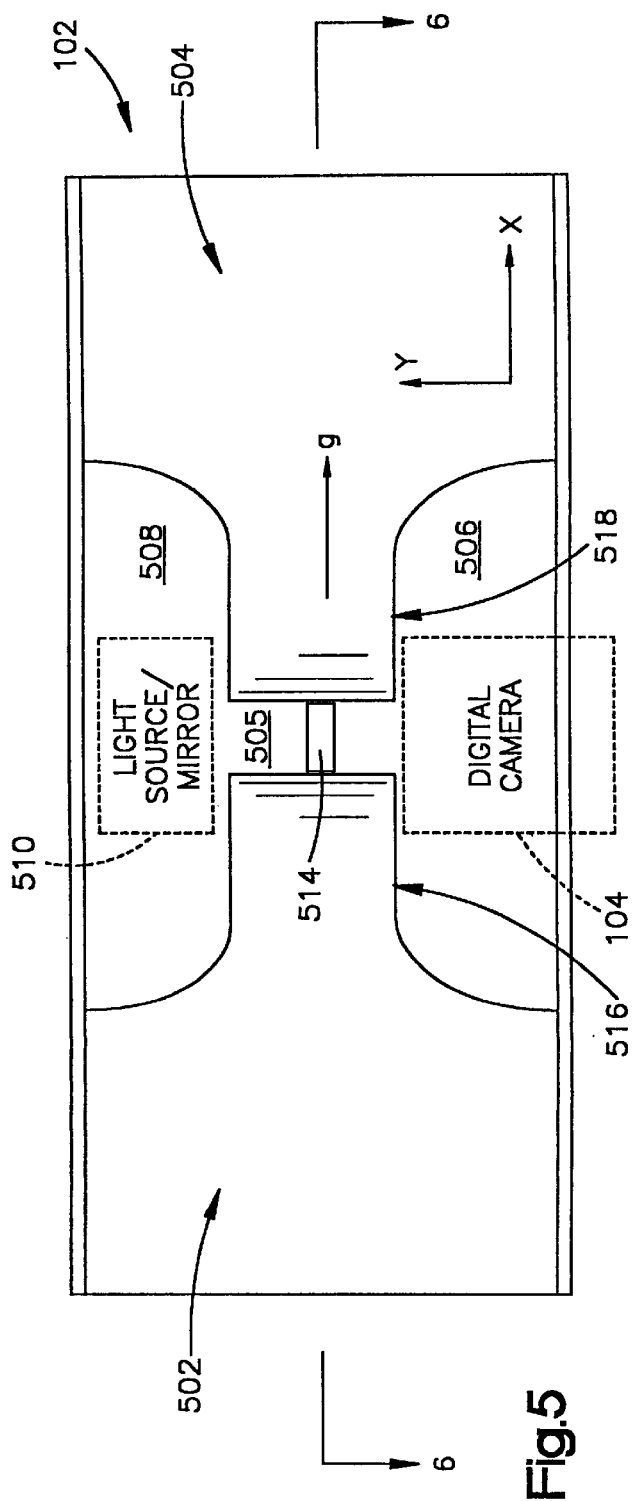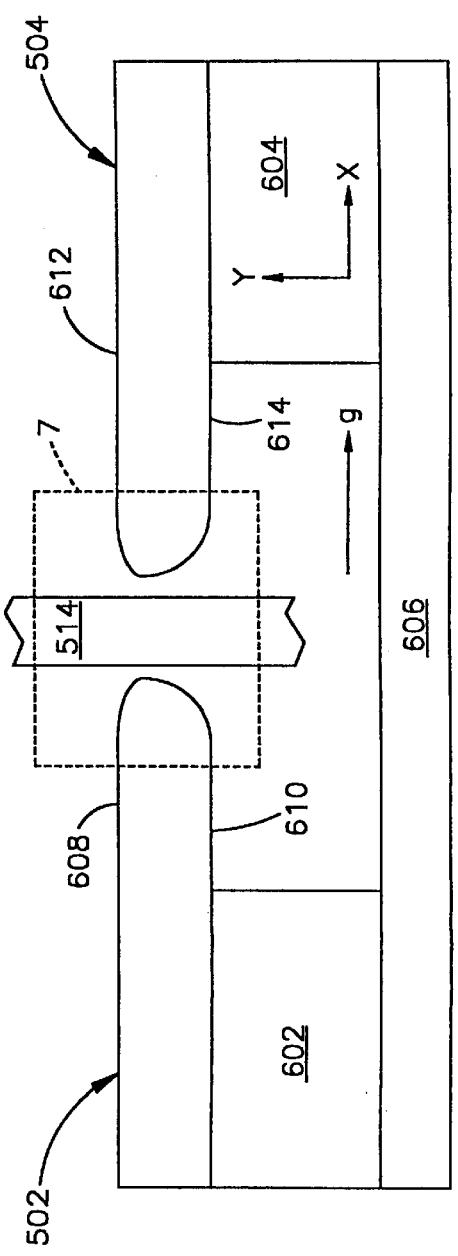
Fig. 5
Fig. 6

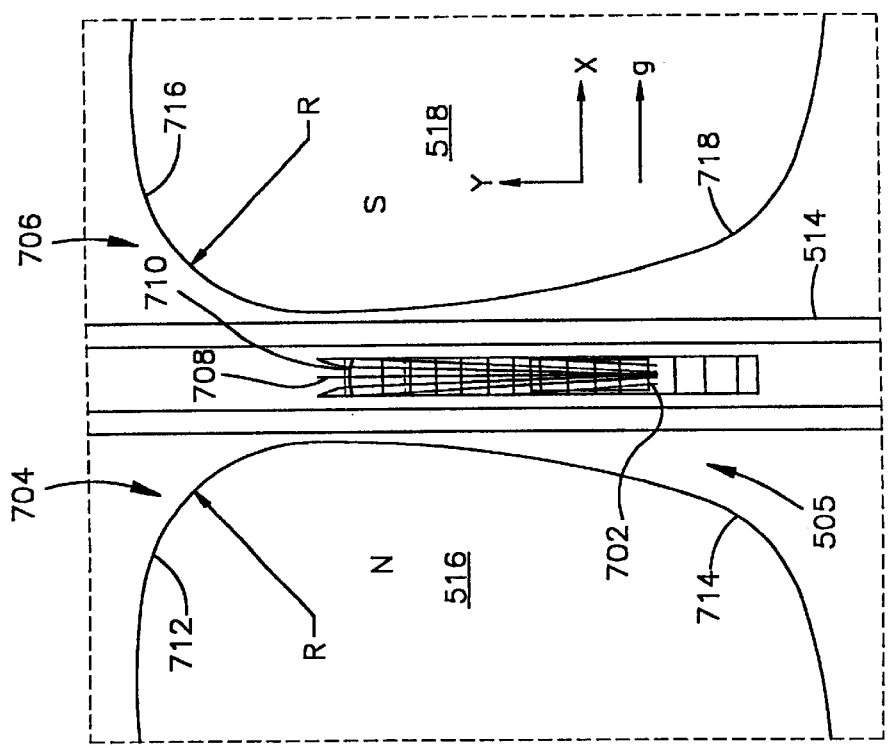
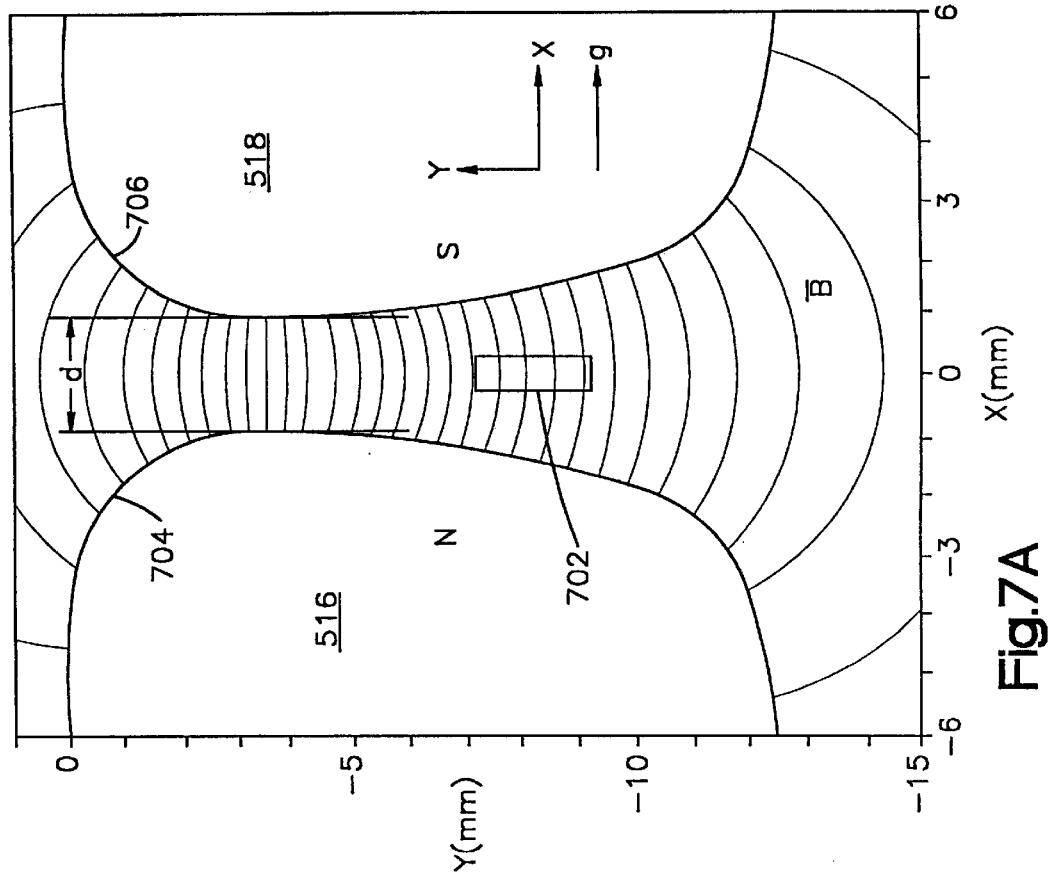
Fig.7A
Fig.7B cd4 labeled lymphocytes
(n=1147)

SYSTEM AND DEVICE FOR DETERMINING PARTICLE CHARACTERISTICS

RELATED APPLICATIONS

This patent application is a Divisional of application Ser. No. 09/020,327, filed Feb. 6, 1998 and titled "System and Device for Determining Particle Characteristics" and now U.S. Pat. No. 6,082,205. This patent application is related to patent application Ser. No. 09/020,339, filed Feb. 6, 1998, titled "Method for Determining Particle Characteristics" which is hereby incorporated by reference and now U.S. Pat. No. 5,910,787.

Federal sponsorship of this invention has been provided by Contract No. CA623349.

FIELD OF THE INVENTION

The invention relates generally to methods and apparatuses for determining particle characteristics, and more particularly, to methods and apparatuses having particle tracking and image analysis logic and force field devices for determining one or more physical cell characteristics.

BACKGROUND OF THE INVENTION

Cell analysis and separation is an increasingly important technique in the diagnosis and treatment of various cancers and diseases. Of primary importance to cell analysis and separation is the ability to identify, or label, cell properties and characteristics of interest. The identification, or labeling, of cell properties and characteristics allows them to be used as "handles" which, in turn, can be used to separate "labeled" cells from other cells. Among the most commonly used labels for sorting cells are immunological labels which include, for example, immunofluorescent and immunomagnetic labels. Immunofluorescent labels typically include, for example, a fluorescent molecule joined to an antibody. Immunomagnetic labels typically include, for example, a paramagnetic compound or molecule joined to either a primary or secondary antibody. Cell labeling is performed by attaching the antibody to a marker of interest on the surface of the cell (i.e., cell surface marker).

However, though extremely sensitive immunological "labels" have been developed which allow for the careful labeling of cells, the potential of these labels for cellular analysis and separation has yet to be fully realized. As a result thereof, the cellular properties and characteristics which these labels are capable of identifying have also yet to be fully analyzed. For example, in the case of immunomagnetic labels, the highly accurate quantification of a cell population's magnetic susceptibility has been impossible to determine. Additionally, in the general case of immunological labels, the cell surface marker and label density has been difficult to accurately determine.

These deficiencies are due, in large part, to the limitations of analytical devices which are capable of gathering and analyzing the information these immunological labels can provide about cells. Moreover, the lack of qualitative and quantitative knowledge of cell properties and characteristics, such as magnetic susceptibility and cell surface marker and label density, hampers the development of sophisticated cell sorting apparatuses. Accordingly, it is an object of the present invention to provide a method and apparatus for qualitatively and quantitatively analyzing one or more cell characteristics or properties.

SUMMARY OF THE INVENTION

According to one aspect of the present invention, apparatuses and methods are provided for quantifying at least one of a plurality of particle physical characteristics. The range of particles includes, for example, cells, cell organelles, platelets, inorganic, organic, biological, and polymeric particles which are optically visible. The plurality of particle physical characteristics include particle size, shape, magnetic susceptibility, magnetic label density, charge separation, dielectric constant, and derivatives thereof. Derivatives include, for example, cell dimensions (e.g., diameter, radius, major axis length, minor axis length, etc.) and optical transmittance. The method includes generating a region of space having a substantially constant force field, determining the velocity of at least one particle within the region by identifying and locating the particle and its coordinates in at least two temporally defined digital images, and determining the at least one of a plurality of particle physical characteristics from the determined velocity and a predetermined force field magnitude and direction.

These steps include several steps or sub-steps. In particular, the step of determining the velocity of at least one particle in a force field includes the step or sub-step of processing the at least two temporally defined digital images so that the particle is distinct from the background of each temporally defined digital image. This step of processing includes one or more of the following steps or sub-steps: histogramming, color stretching, filtering, background subtraction, identifying contrast differences. The step of determining the velocity of at least one particle in a force field further includes the step or sub-step of tracking the location of the particle through the at least two temporally defined digital images by determining at least one predicted path and the distance the particle has traveled. Other steps or sub-steps are more fully set forth in the detailed description.

According to another aspect of the present invention, a device for determining one or more particle physical characteristics is also described. More specifically, the device has a force field device for subjecting at least one particle to at least one force field, a substantially transparent flow channel, and a computer system for gathering and analyzing data associated with the at least one particle. The force field device has, among other things, a first and second force field producing assembly. Each assembly has a force field producing device and a pole piece for concentrating the force field flux. The pole pieces each have a flux concentrating portion having a curved end portion for producing a region of space having a substantially constant force field and wherein the flux concentrating portions are displaced substantially opposite each other with an inter-polar air gap therebetween. The substantially transparent flow channel is positioned at least partially within the region of space and provides for the introduction of at least one particle thereinto. A flow system having a pump for controlling flow into the channel is also provided.

According to another aspect of the present invention, a system for determining one or more particle physical characteristics is provided. The system has a force field device for generating at least one force field having a predetermined force field magnitude and direction and for subjecting at least one particle to the at least one force field, a flow system for regulating the introduction of the at least one particle into the force field device, and a computer system for gathering and analyzing data associated with the at least one particle. The computer system has, among other things, a digital image system for acquiring at least two temporally defined digital images of the at least one particle, logic for identifying and locating the at least one particle and its coordinates within the at least two temporally defined images, logic for determining the velocity of the at least one particle within the force field, and logic for determining at least one particle physical characteristic from the determined velocity and the predetermined force field magnitude and direction.

According to yet another aspect of the present invention, a pole piece assembly for producing a region of space having a substantially constant magnetic force field is provided. The assembly has, among other things, a first pole piece having a substantially curved flux concentrating portion, a second pole piece having a substantially curved flux concentrating portion, and a device for producing a magnetic flux in flux communication with the first and second pole pieces. The first and second pole pieces are configured to form an inter-polar air gap. The substantially curved flux portions of the first and second pole pieces each have a first distal end having a curved portion and a second distal end having a curved portion. The curved portion of the each first distal end includes a predetermined radius and the curved portion of the each second distal end includes an approximately hyperbolic function, wherein the hyperbolic function is defined by the function $y(x)=9.544/x^2-12.719$, where x and y are Cartesian coordinates (preferably in millimeters) with the origin placed at the intersection of the plane of symmetry separating the pole pieces and a plane tangent to the radial portion of the distal ends of the pole pieces.

It is, therefore, an advantage of the present invention to provide an analytical tool for analyzing and measuring at least one of a plurality of particle characteristics.

It is another advantage of the present invention to provide a region of substantially constant magnetic force for application to at least one magnetically susceptible particle.

It is another advantage of the present invention to provide a computer system having logic for analyzing and measuring the magnetic susceptibility of at least one magnetically susceptible particle.

Further advantages will become apparent from a consideration of the ensuing description and drawings.

BRIEF DESCRIPTION OF THE DRAWINGS

In the accompanying drawings which are incorporated in and constitute a part of the specification, embodiments of the invention are illustrated, which, together with a general description of the invention given above, and the detailed description given below, serve to example the principles of this invention.

FIG. 2 is a high-level flowchart of the overall Particle Tracking Velocimetry Analysis logic;

FIG. 3 is a flow chart illustrating the image processing logic of the present invention;

FIG. 4 is a diagram of the two-dimensional cell tracking function of the present invention;

FIG. 5 is a top plan view of one embodiment of a force field device of the present invention;

FIG. 6 is a cross-sectional view taken on section line 6—6 of FIG. 5 of the force field device of the present invention;

FIG. 7A is a graph showing the magnetic field lines generated by the present invention;

FIG. 7B is a magnified view of a portion of the force field device of FIG. 6;

DETAILED DESCRIPTION OF ILLUSTRATED EMBODIMENT

Figure 1:
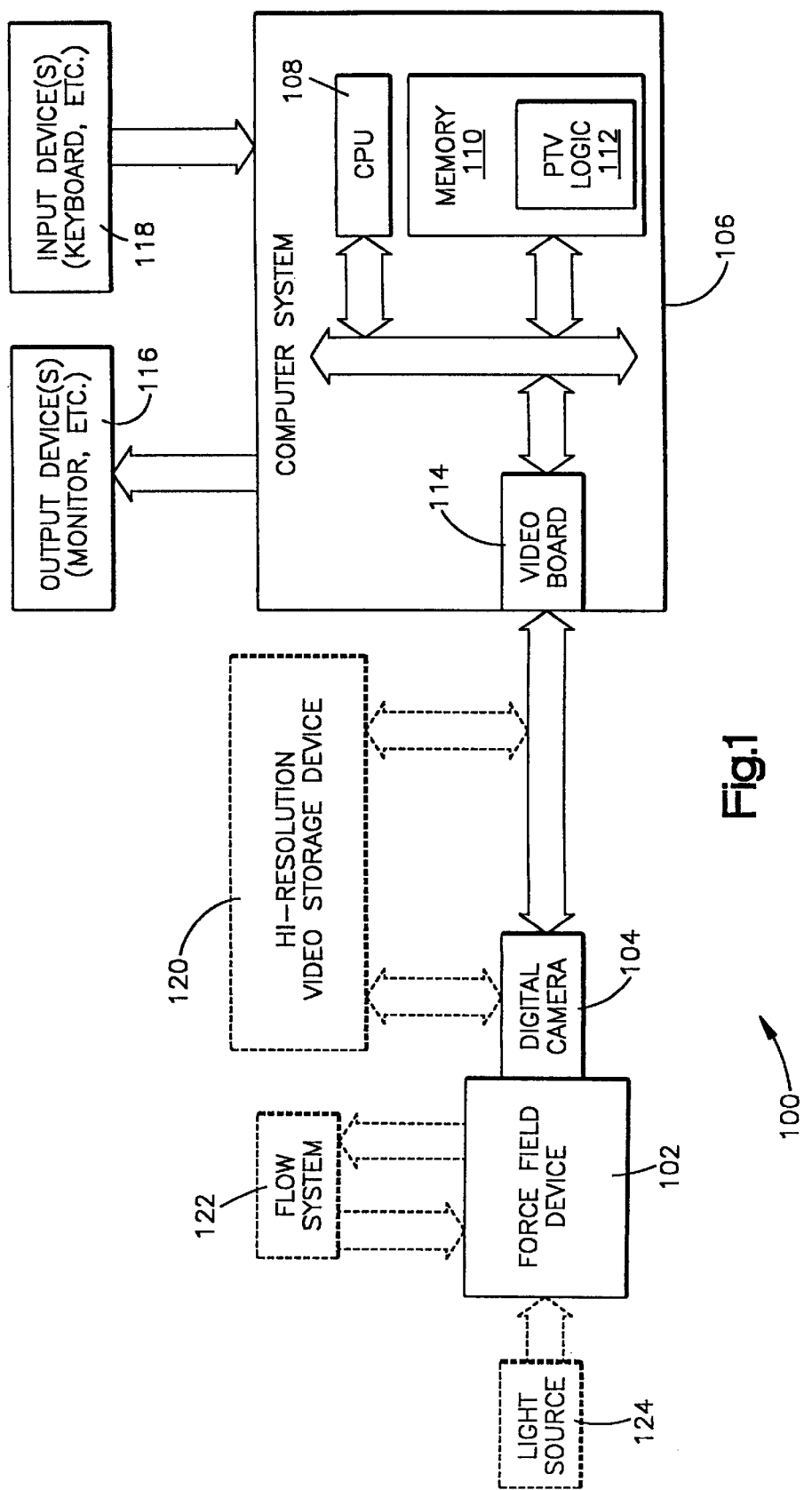
FIG. 1 is a high-level functional block diagram of a quantitative analysis device 100 of the present invention.

Referring now to FIG. 1, a high-level functional block diagram of a quantitative analysis device 100 of the present invention is shown. The device 100 has a force field device 102, digital or analog camera 104, computer system 106, input device(s) 118, and output device(s) 116. The computer system 106 contains a CPU 108, memory 110, Cell Tracking Velocimetry analysis logic 112 (hereinafter CTV logic 112), video board 114, and various other support devices including, for example, floppy, hard, and CD-ROM drives, fax/modem, interface logic, etc. (not shown). The CPU 108 is preferably a CPU which is capable of quickly and efficiently processing large amounts of graphical information. One such CPU is the Intel MMX® microprocessor. However, other microprocessors may also be employed such as, for example, the Intel Pentium® processor, Intel 80486, or other high-performance microprocessors. One such computer system having the above-described features, or easily modifiable to have the above-described features is, for example, an IBM APTIVA® or Gateway 2000® personal computer system with an Intel MMX® microprocessor.

The video board 114 of the present invention preferably has the ability to capture and process high resolution video and image information from external devices (e.g., digital or analog cameras) or internal devices (e.g., built-in video tuner). The video board 114 preferably contains a video processor, video memory and various interface logic for interfacing to digital and/or analog cameras, display devices, and the computer system 106. One such suitable video board 114 is the P360F Power Grabber manufactured by DPIX Technologies Inc. Other high performance video boards having similar characteristics may also be employed. The output device(s) 116 include(s), for example, display monitors, printers, and external storage devices. The input device(s) 118 include(s), for example, a keyboard, mouse, and voice input. Other input/output devices may also be employed.

The digital camera 104 preferably contains the ability to capture high-resolution monochrome and/or color video and still-image information. A suitable digital camera is. for example, the CCD 4915 camera, manufactured by Cohu Inc. of San Diego, Calif., with a 2.5× and a 6.7× magnification insert. Other cameras having similar characteristics may also be employed. Additionally, magnifications other than 2.5× or 6.7× may also be utilized, depending on the size of the cells or particles being analyzed and the required magnification. In the alternative, a high-resolution video storage device 120 such as, for example, a sVHS video recorder or optical disk(s) may be employed to store the video and images for subsequent analysis and archiving. Additionally, a light source 124 may be employed to improve image quality. The light source 124 may be a source coherent light of one or more wavelengths such as, for example laser light, or non-coherent light of one or more wavelengths such as, for example, white light, colored light, ultra-violet light, or infra-red light, or combinations thereof The force field device 102 is responsible for a number of important functions within the present invention. Firstly, the force field device 102 allows the cells or particles to be subjected to and displaced by a force field. Secondly, the force field device 102 allows for the cell or particle displacement to be viewed and/or captured by the digital camera 104. Thirdly, the force field device 102 may, in certain embodiments, provide the force field being applied (e.g., a magnetic field). Other functions will also be apparent from the detailed discussion presented below.

Particle Tracking Velocimetry Analysis Logic.

The CTV logic 112 of the present invention analyzes a plurality of closely-timed cell or particle images to determine, among other things, individual cell or particle locations and velocities through each captured image. All the data collected and determined by the CTV logic, including the captured image information, is preferably stored in a database for subsequent viewing, analysis, or review. As will be described in more detail, once the cell locations and velocities are known, many other characteristics such as, for example, cell acceleration, force, and mass may be determined therefrom. It should also be noted that the CTV logic 112 is not dependent upon the specific type of force field applied to the cells or particles. Therefore, the CTV logic may be employed in systems where the force field device is employing magnetic, electric, or gravitational fields. The present discussion will hereinafter focus on the analysis of cells; however, it should be noted that the discussion is equally applicable to other particles such as, for example, cell organelles, and other metallic/non-metallic particles.

Referring now to FIG. 2, a flow chart 200 of the overall CTV logic 112 is shown. The CTV logic begins in step 202 where the digital camera 104 (shown in FIG. 1) acquires a number of images. Firstly, the digital camera 104 acquires at least one background image. A background image is an image of the observation area of the force field device 102 which typically contains a glass tube or channel through which cells are or will be visible. The background image is used in a background subtraction function of the image processing logic. See the text associated with FIG. 3 for a detailed discussion of the background subtraction function. Secondly, the digital camera 104 acquires a plurality of closely timed digital images of the cells. Each digital image is acquired at an image sampling rate generally in the range of 15 to 60 Hz, with a preferable image sampling rate of 30 Hz. These digital images are also known as, and commonly referred to as, an image "frame" or "frames." The video board 114 converts each pixel of each image frame into one of a plurality of digital image formats which convey pixel brightness and/or color information. The digital formats range from 8 to 24 bits of information per pixel. The preferred image format is 8 bits of gray-level information per pixel. The 8 bits of gray-level information provide a range of gray-level values from 0 (i.e., black) to 255 (i.e., white).

Each image frame contains a high-resolution pixel array, preferably in the general range of 600×400 to 1280×1024 pixels. The digital camera of the illustrated embodiment provides a high-resolution 624×450 pixel array. Moreover, the digital image sampling rate of 30 Hz may be increased or decreased depending on the required image frame resolution. For example, the sampling rate of 30 Hz produces 30 image frames per second. If a higher image frame resolution is required, the sampling rate may be increased to, for example, 60 Hz (i.e., 60 image frames per second.) Similarly, if a slower image frame resolution is acceptable, the sampling rate may be decreased to, for example, 15 Hz (i.e., 15 image frames per second.) After the image frames are acquired in step 202, the CTV logic advances to step 204 where the image frames are processed for standardization which facilitates the tasks of locating and identifying individual cells and determining their velocities.

Referring now to FIG. 3, a flow chart 300 illustrating the image processing logic of the present invention is shown. Generally, the acquired physical images from the digital camera 104 are not optimal for cell tracking because the gray-level differences between the background image and the cell image(s) are not distinct. Accordingly, some degree of image processing is required. The task of locating and identifying cells and their velocities is facilitated by processing the image frames so that they contain only bright cell images and a dark background image, and it is a primary function of the image processing logic to achieve this result, or very near thereto. To this end, the image processing logic executes a plurality of steps including, but not limited to, for example, listogramming, stretching, spatial filtering, background subtraction, pattern filtering, and pixel size matching.

Accordingly, the image processing logic starts in step 302 where a histogramming function is executed for each image frame. Histogramming is a statistic measure of the frequency of the gray-level versus the gray-level itself. The range of gray-level is from 0 (i.e., black) to 255 (i.e., white) for an 8-bit gray-level image. Therefore, by histogramming the gray-levels of an image frame, a range of dominant gray-levels may be determined from the frequency of their occurrence. The range of dominant gray-levels, in turn, indicate whether the cell image is distinct from the background image of the image frame. For example, if the range of dominant gray-levels fall between 175 and 250, it can be said that the cell image is not distinct from the background image. However, if the range of dominant gray-levels comprises two sub-ranges with one sub-range localized near the gray-level of 0 (i.e., black), for example, and the other sub-range localized near the gray-level of 255 (i.e., white), for example, then it can be said that the cell image is distinct from the background image of the image frame. It should be noted that whether the cell image is distinct from the background image is a matter of degree. In an ideal image frame, the cell image would appear white in color (i.e., gray-level 255) and the background image would appear black in color (i.e., gray-level 0). It is a goal of the image processing logic to standardize all image frames as close as possible to this norm.

After step 302, the image processing logic advances to step 304 where a stretching function is executed for each image frame. The stretching function is employed when the distribution of the gray-level in the image frame does not cover the full brightness range and produces poor contrast between the cells and the background. The stretching function is accomplished by setting a minimum and a maximum gray-level value. The minimum gray-level value is set to the low-end and the maximum gray-level value is set to the high-end of the general range of dominant gray-level values as determined by the histogramming function. In the stretching function, all image frame pixels with a gray-level value less than the minimum gray-level value are set to 0 (i.e., black). All image frame pixels with a gray-level value greater than the maximum gray-level value are set to 255 (i e., white). All image frame pixels with gray-level values in the range between the minimum and maximum are stretched proportionally, to a value between 0 and 255, based on their original gray-level value. The result of the stretching function is an image frame that contains distributions of gray-level values which distinctly correspond to the cell images and the background image. After step 304, the image processing logic advances to step 306.

In step 306, the image processing logic executes a low-pass spatial filtering function for each image frame. The low-pass spatial filtering function removes small details, or noise, from the image frame. Low-pass spatial filtering is also known as "neighborhood averaging" and is used to reduce noise by smoothing local gray-levels of the image. After step 306, the image processing logic advances to step 308.

Since the CTV logic requires image frames which contain only bright cell images and a dark background image, a background subtraction function is executed for each image in step 308. The background subtraction function is particularly useful because most experimental systems include extraneous matter such as, for example, dirt on the surfaces of camera lenses and other observation devices such as, for example, glass tubes or channels. In the background subtraction function, an image frame of the background is subtracted from the image frame containing the cell images and the background image. To recall, one of the first images acquired in step 202 of FIG. 2 is an image of the background of the scene where the cells will eventually appear. That is, the background image is an image of the observation area of the force field device which typically contains a glass tube or channel through which cells will be visible. Accordingly, after the background subtraction function in step 308 is performed, each image flame generally contains bright cell images and a dark background image.

After step 308, the image processing logic proceeds to step 310 where a cell template function is applied to each cell of each image frame. A cell template is a standard complete cell image which has been pre-defined based on an actual physical image of the cell. The need to apply the cell template function arises because, after image processing, the cell images may appear as hollow spheres with their interiors having the same gray-level as the background image. Consequently, after application of the cell template function, the cell images no longer appear as hollow spheres but as solid bright spheres. It should be noted that application of the cell template function may be optional because after image processing, some cell images may already appear as solid bright spheres. Therefore, in such cases there would be no need to apply the cell template function.

Referring now once again to FIG. 2, after the image processing of step 204 has been completed, the CTV logic advances to step 206. In step 206, two-dimensional cell identification and location is performed for each image frame. This step involves the separation of cell images from the background image and the determination of cell location within the image frame. Cell locations are identified based on the contrast difference between the cell image and the background image. The cell image is defined as a shape connected set of pixels having an intensity greater than a given threshold gray-level value. The threshold gray-level value can fall within a range of possible values such as, for example, 0 (i.e., black) to 79. Therefore, in the given example, all pixels having a gray-level value greater than 79 would have an intensity greater than the given range of threshold gray-level values and would, therefore, be interpreted as belonging to a cell image. This result is achieved by scanning the pixels of each image frame and determining whether their intensity is greater than the threshold value.

Once the cell images have been identified, the CTV logic determines the location of the center of each cell within each image frame. This process is facilitated by using the pixel array of each image frame as a coordinate system. Additionally, since each cell image is a solid sphere, or very nearly thereto, the center of the cell image is easily determined by locating the center of the sphere, which appears as a circle in two-dimensions. These locations are stored in a database for use in the two dimensional cell tracking function of step 208. Additionally, the CTV logic may include a function which allows for the entry of minimum and maximum cell size and aspect ratio data as a criteria for further cell image recognition.

In step 208, the CTV logic executes the two-dimensional cell tracking function. This function employs a sequence of five image frames to establish, therefrom, the most probable path (as a function of time) taken by each cell. The most probable path determination is based on the concept of "path coherence." Generally, the concept of "path coherence" holds that cell position, velocity, acceleration, change of acceleration, etc., are internally self-consistent and that these characteristics can be described by mathematical functions that are smooth.

The two-dimensional cell tracking function of step 208 will now be described with reference to FIG. 4. Illustrated in FIG. 4 are the positions of a single cell as determined from three consecutive image frames. The position of the cell in the first image frame is indicated by C1, in the second image frame by C2, and in the third image frame by C3. Starting with the cell C1 in the first frame, a search radius "r" is established, thereby establishing search area 402, and will be used for identification of cell images in the second image frame. The value of the search radius "r" is dependent on a number of factors including, for example, image sampling frequency and cell displacement between image frames. Therefore, if the cell displacement between image frames is relatively small, a small search radius "r" can be used. For example, "r" can be somewhere in the general range of 1 to 3 times the cell diameter. The ascertained cell diameter is preferably in the range of 1 $\mu$m or greater. However, if the cell displacement between image frames is relatively large, a larger search radius "r" would be required (e.g., greater than the general range of 1 to 3 times the cell diameter). The same search radius "r" is established for every cell of an image frame.

Accordingly, once the search radius "r" has been established in the first image frame, all cells in the second image frame within the search radius are tagged and identified. As shown in FIG. 4, cell image C2 is within the search radius and search area 402. Since the coordinates of the center of cell image C2 are known, the distance D1 and vector direction from cell image C1 can be determined. These values are used to determine a candidate path 404 for the cell. Therefore, from the first and second image frame, the path and location of the cell in the third frame is predicted (shown at point "P" on predicted path 404). Once predicted, the path and location of the cell is compared to the actual position of the cell image C3 in the third frame. After comparison, the error between the predicted (i.e., point "P") and actual cell image position C3 is determined and added to a penalty function. The penalty function is a measure of path coherence. That is, the smaller the penalty function, the greater the path coherence. Therefore, the error between cell images C1 and C2 is zero by default since at least 2 points are required for a path. However, an error may exist, as shown in FIG. 4, between the predicted third image frame cell location (i.e., point "P" on predicted path 404) and the actual third image frame cell location C3. Since the coordinates for the predicted cell location "P" and the actual cell location C3 are known, an error value may be determined therefrom.

This procedure is repeated with the fourth image frame using the data acquired from the first three image frames and, similarly, for the fifth image frame using the data acquired from the first four image frames. As may be the case, the CTV logic may have to analyze several possible paths if more than one cell image has been tagged and identified within a search radius. In such situations, the values of the penalty functions for each separate possible path are compared and the path with the smallest penalty function value is chosen as the correct path. Once the image frames have been analyzed sequentially from the first image frame to the fifth image frame, the process is reversed and the image frames are analyzed sequentially starting with the fifth image frame to the first image frame. This allows for the consideration of any biases which may be caused by the order of image frame analysis.

Specifically, the bias value is a measure of reliability that a determined cell path is the correct cell path. For example, if drastic differences between the forward analysis penalty function value and the reverse analysis penalty function value are present, a large bias in one of the two directions of analysis exists—thereby indicating that the presently determined cell path may be less reliable than other potential candidate cell paths. Similarly, a small bias value would indicate that the presently determined cell path is more reliable than other potential candidate cell paths. Accordingly, cell paths having small penalty function values and small, or no, bias values are reliable as determined or most probable cell paths.

Hence, by knowing the location of each cell from image frame to image frame and the time between image frames (i.e., sampling frequency), a number of cell characteristics can be determined by the CTV logic 112 such as, for example, the velocity of the cell from image frame to image frame. Furthermore, since the velocity of the cell is known at a plurality of different times, the acceleration of the cell can also be determined. Still further, if the mass of the cell is known, the force acting on the cell can be determined or vice-versa. Therefore, the CTV logic of the present invention can determine a wide range of physical parameters including, for example, all of the above-mentioned parameters and values. Additionally, depending on the type of force field device 102 being employed, particle physical characteristics such as, for example, magnetic susceptibility, charge cell separation and size, may be determined from the above physical parameters and values. For all of the data collected, the CTV logic 112 can determine an average value, the standard deviation, and the range for the cell population analyzed through a plurality of known means. These values are the ultimate outputs of the CTV logic 112 and may be output to a display monitor, printer, or storage device.

Force Field Device.

As already mentioned, the force field device 102 (shown in FIG. 1) provides a number of important functions within the present invention such as, for example, allowing the cells to be subjected to and displaced by a force field and allowing for cell displacement to be viewed and/or captured by a camera. The force field device 102 of the present invention may employ any one of a variety of force fields including, for example, flow, magnetic, electric, and gravitational fields. One illustrated embodiment of a force field device 102 employing a magnetic field is shown in FIGS. 5, 6, 7A, and 7B. Through the use of a magnetic field, the present invention can determine, for example, the magnetic susceptibility of cells. Once determined, the magnetic susceptibility can be used to appropriately design magnetic field(s) and the magnetic assemblies of cell sorting devices. This is of particular importance for fractional cell sorting devices which sort cells based on the density of magnetically labeled cell surface markers.

Referring now to FIGS. 5 and 6, a force field device 102 for subjecting cells to a magnetic force field is shown. FIG. 5 is a top plan view and FIG. 6 is a cross-sectional view taken on section line 6—6 of FIG. 5. Force field device 102 includes a base 606, two pairs of force field producing magnets 602 and 604, and two pole pieces 502 and 504. The magnets 602 and 604 are generally rectangular in shape and preferably in the range of about 2"×2"×1" and preferably made from a permanent magnetic material such as, for example, a neodymium-iron-boron alloy. The base 606 and the pole pieces 502 and 504 are preferably made from a material that is capable of having a magnetic flux induced therein such as, for example, 1018 low-carbon cold-finished steel. The pole pieces 502 and 504 each have a flux concentrating portion 516 and 518, respectively, and top and bottom surfaces 608 and 610, respectively. The distance between top and bottom surfaces 608, 610 and 612, 614, is approximately in the range of 12–13 mm, with a preferred distance of approximately 12.5 mm.

The base 606, magnets 602 and 604, and pole pieces 502 and 504 are assembled as shown in FIGS. 5 and 6 so as to form an inter-polar air gap 505 and utility spaces 506 and 508. If necessary, utility space 506 may be used for placing the digital camera 104 in close proximity to the inter-polar air gap 505. Similarly, utility space 508 may be used for providing a light source or mirror 510 which directs light through the inter-polar air gap 505. A channel 514 is positioned within the inter-polar air gap 505 such that cells therein are subjected to a substantially uniform magnetic field. The channel 514 is made from an optically clear invert material such as, for example, borosilicate glass. The channel 514 is substantially rectangular in cross-section.

Referring now to FIG. 7A, a graph showing the magnetic field lines versus x and y position generated by the present invention is illustrated. In particular, the location of the region of constant magnetic force 702 is shown relative the inter-polar air gap, along with the magnetic field lines B.

Referring now to FIG. 7B, a magnified view of portion 7 of FIG. 6 is shown. The flux concentrating portions 516 and 518 have end surfaces 704 and 706. End surfaces 704 and 706 each have curved distal ends 712, 714 and 716, 718, respectively. Curved distal ends 712 and 716 have a radius in the general range of 3 mm with a preferable radius of 3.18 mm. Curved distal ends 714 and 718 are generally hyperbolic and preferably defined by the hyperbolic function:

$$y(x)=9.544/x^2-12.719$$

where and y are Cartesian coordinates, preferably in millimeters, with the origin placed at the intersection of the plane of symmetry separating the pole pieces and a plane tangent to the radial portion of the distal ends of the pole pieces. In the preferred embodiment. distal ends 712 and 714 are configured such that they are continuous with each other. Distal ends 716 and 718 are also similarly configured. However, in alternate embodiments, an approximately linear surface may be provided between distal ends 712 and 714 so as to also provide a continuous joinder of the distal ends. Distal ends 716 and 718 may also be similarly joined by an approximately linear surface.

The channel 514 is preferably placed within the inter-polar air gap 505 such that it is very nearly in physical contact with the end surfaces 704 and 706. Alternatively, the channel 514 may be placed in actual physical contact with end surfaces 704 and 706. The width of the inter-polar air gap 505 is, at its narrowest, approximately 2 mm. So configured, the force field device 104 generates a region 702 of substantially constant magnetic force which is exerted onto the cells present within this region. The gradient of the magnetic field energy ($\nabla(B^2/2\mu_0)$) is generally illustrated at 708 and the constant magnetic energy lines ($B^2/2\mu_0$) are generally illustrated at 710.

Figure 8:
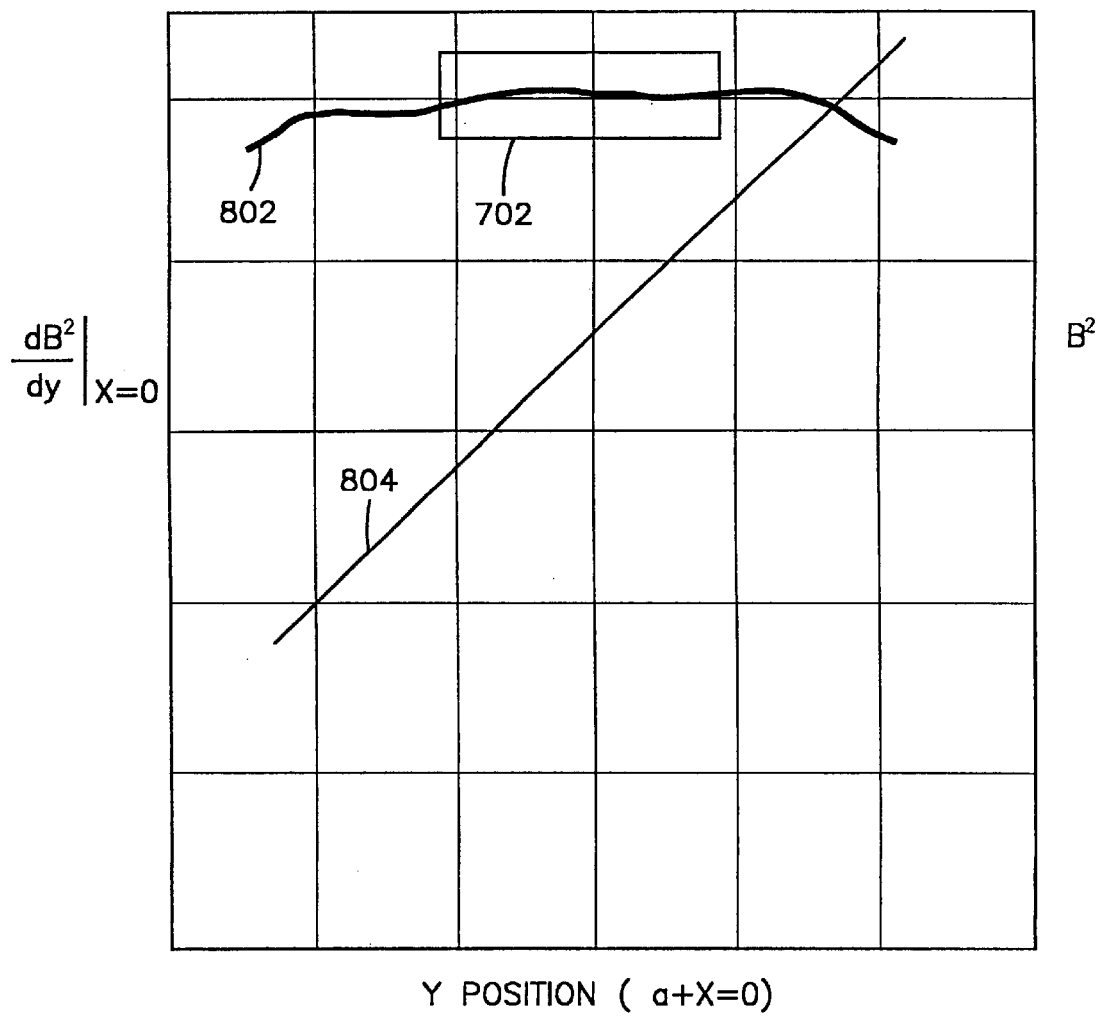
FIG. 8 is a graph illustrating the magnetic force and rate of change of magnetic force versus y-axis position of the force field device of FIGS. 5, 6, and 7.

Referring now to FIG. 8, a first graph 804 illustrating the magnetic energy $B^2/2\mu_0$ versus y-axis position (at x=0) of the force field device of FIGS. 5, 6, 7A and 7B is shown and a second graph 802 illustrating the rate of change of the magnetic energy $B^2/2\mu_0$ with respect to the y-axis position at x=0 (i.e., the derivative $dB^2/dy$) is also shown. The region 702 of FIG. 7B is generally indicated in FIG. 8 and falls within the general range of −7.5 to −9.5 mm from the top of the pole pieces 502 and 504. It should be noted that changes in pole piece geometry will affect the y-axis position of the substantially constant magnetic force region 702.

The force field device 102 of the present invention is in fluid communication with a flow system 122 (shown in FIG. 1) which provides for the injection of cells and a carrier medium into the channel 514 and the flow field. The flow system preferably contains a disposable injection syringe pump which is in fluid communication with the channel 514 via silicone tubing. The other end of the channel 514 is in flow communication with a waste vessel also via silicone tubing. In the alternative, the inlet portion of channel 514 may be in fluid communication with an injection device such as, for example, a disposable syringe pump, and the exit portion of the channel 514 may be fluid communication with an aspirating device such as, for example, an aspirating syringe pump. The flow rate generated by the two pumps being controlled by the computer system 106 or other control logic within the pumps.

As mentioned above, the present invention may be used to determine a plurality of cell characteristics including, for example, cell size and magnetic susceptibility. The following, discussion will now focus on these two examples: Determination of Cell Size based on Cell Settling Velocities.

For a spherical particle settling at terminal velocity, it can be shown from Stokes' law that the diameter of the spherical particle $D_c$ is related to the its velocity $V_c$ by the following equation (1):

$$D_c = \left[\frac{18\eta V_c}{g(\rho_c - \rho)}\right]^{1/2} \quad (1)$$

where $\eta$ is equal to the viscosity of the fluid, $\rho_c$ is the density of the cell, $\rho$ is the density of the fluid and g is 9.8 m/s² for gravity. Hence, the present invention can be used to determine data from which equation (1) can be solved for the cell diameter $D_c$.

Figure 9A:
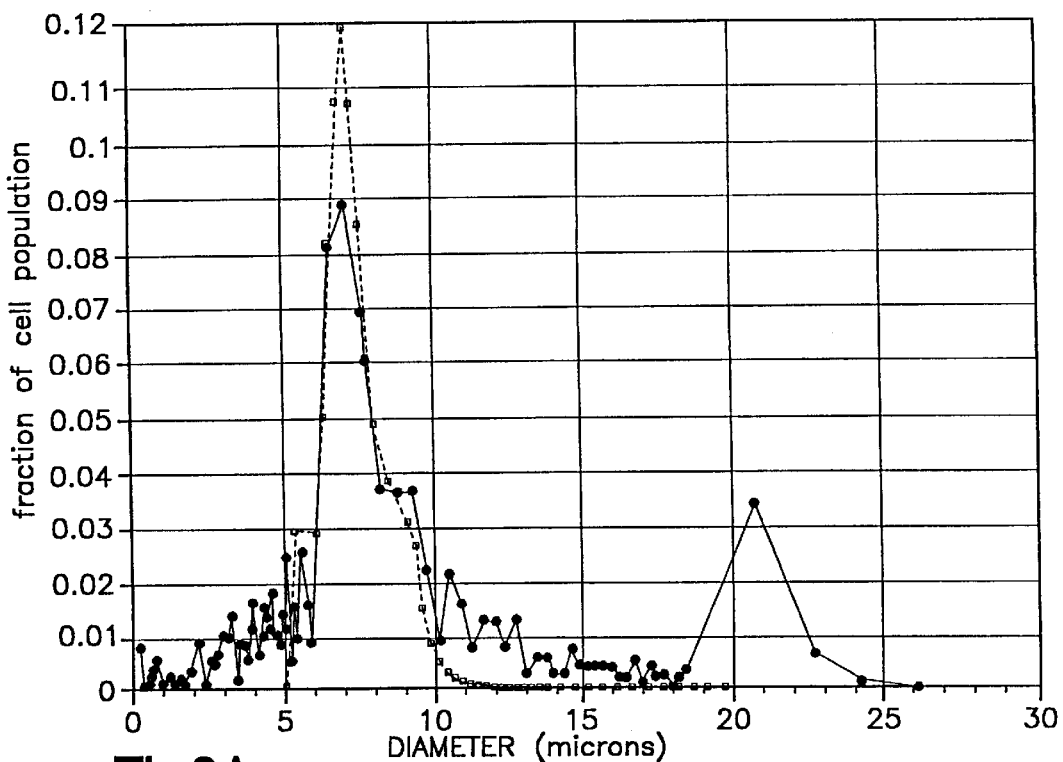
FIG. 9A is a graph showing the distribution of average cell diameters of lymphocyte cells as determined by the present invention and as determined experimentally via a Coulter Multisizer II.

More specifically, the CTV logic analyzes captured images of cells which are subjected to only a gravitational force field (as opposed to an electric or magnetic force field) and determines the cell settling velocities therefrom. Once the cell settling velocities $V_c$ are known, along with the other values of Equation (1), the diameter of the cell $D_c$ is determined. Illustrated in FIG. 9A is a graph showing the distribution of cell diameters of lymphocyte cells as determined by the present invention (i.e., solid line) and as determined experimentally via a commercial cell sizing device (i.e., a Coulter Multisizer II). The Coulter Multisizer II was used to determine cell diameter $D_c$. It should be noted that the primary peak and shoulder generated by each method are in close agreement with each other. The large peak around 20×10⁻⁶ m corresponds to clumps of cells which can be observed visually. The CTV logic of the present invention can also be modified to reject anomalies such as, for example, unreliable or erroneous data.

Determination of Magnetic Susceptibility based on Cell Velocities.

The concept of sorting materials based on their magnetic responsiveness was first introduced in the industrial and mining arts. These methods relied on the intrinsic magnetic properties of the sorted material (generally, iron (i.e., magnetic) from non-iron parts (i.e., non-magnetic)) as a basis of operation. See U.S. Pat. No. 2,056,426 issued to Frantz, "Magnetic Separation Method and Means," in 1936. However, most cells are not intrinsically magnetic or paramagnetic. To overcome this deficiency, magnetic antibodies have been developed which render cells paramagnetic. Accordingly, the ability to separate a cell based on magnetic forces is dependent on the ability to impart onto the cell a paramagnetic label.

A cellular labeling complex generally contains a cell having a surface antigen or marker, e.g., protein(s), which serve as a marker to which a magnetic antibody can be attached. Other cellular labeling complexes are also possible. For example, one may attach a fluorescent label which includes a primary antibody—fluorescein conjugate to a surface marker and a secondary antibody—magnetic label conjugate to the primary antibody. The primary advantages of this type of cellular labeling complex is that it allows for additional analysis by FACS (Fluorescence-Activated Cell Sorting) systems and the analysis of cell motion using ultra-violet light. Other suitable labeling complexes include, for example, high or low density labels (e.g., high density metal particles such as gold, or low density particles such as polymeric particles), electrically-charged labels (e.g., ions) or combinations of all of the aforementioned types of labels. Consequently, once a homogeneous cell population has been paramagnetically labeled, it may be separated from a heterogeneous cell population.

The magnetic antibody may be of a plurality of types. More particularly, magnetic antibodies can be classified into three broad categories which are based on size: Particulate labels, Colloidal magnetic labels and Molecular magnetic labels. Particulate labels are the largest in relative size to the other labels and Molecular magnetic labels are the smallest in terms of relative size. Additionally, cells may be rendered paramagnetic by binding a specific paramagnetic compound to a specific hapten on a cell or the specific or non-specific binding of a paramagnetic metal or metal complex directly to a cell (i.e., metal binding microorganism or by phagocytosis). Therefore, it should be apparent to those skilled in the art that a cell may be rendered paramagnetic by a number of ways. While under the proper desilgn specifications any of the three types of magnetic labels can be suitable, the present invention preferably employs either colloidal magnetic labels or molecular magnetic labels.

As mentioned, once a homogeneous cell population has been paramagnetically labeled, it may be separated from other non-paramagnetic cell populations within a heterogeneous cell population. The separation of paramagnetic cells from non-paramagnetic cells is commonly referred to as binary separation. However, because the degree to which a paramagnetic label binds to a cell (i.e., magnetic susceptibility) may vary significantly within a given heterogeneous cell population, and sometimes even within a homogeneous cell population, the opportunity to fractionally sort the paramagnetically labeled cell population into paramagnetic sub-populations has arisen. Accordingly, knowledge of the average magnetic susceptibility of a homogeneous cell population, along with the standard deviation and range, is required in the design of such fractional cell sorting devices.

In particular, it can be shown that the magnetic susceptibility $\Delta\chi$ of a labeled cell migrating in a magnetic field is given by equation (2):

$$\Delta\chi = \frac{V_C 3\eta\mu_0}{D_C \alpha\beta \frac{dB^2}{dy}\Big|_{x=0}} \quad (2)$$

where $\mu_0$ is permeability of free space, $V_c$ is velocity of the cell, $D_c$ is cell diameter, $\alpha$ is cell surface marker density, $\beta$ is number of magnetic labels bound per cell surface receptor site, and B is the magnetic flux density. Equation (2) can be solved for the either the magnetic susceptibility $\Delta_\chi$ or the cell surface marker density $\alpha$ through the proper use of controls and independently determined values for the other variables.

Figure 9B:
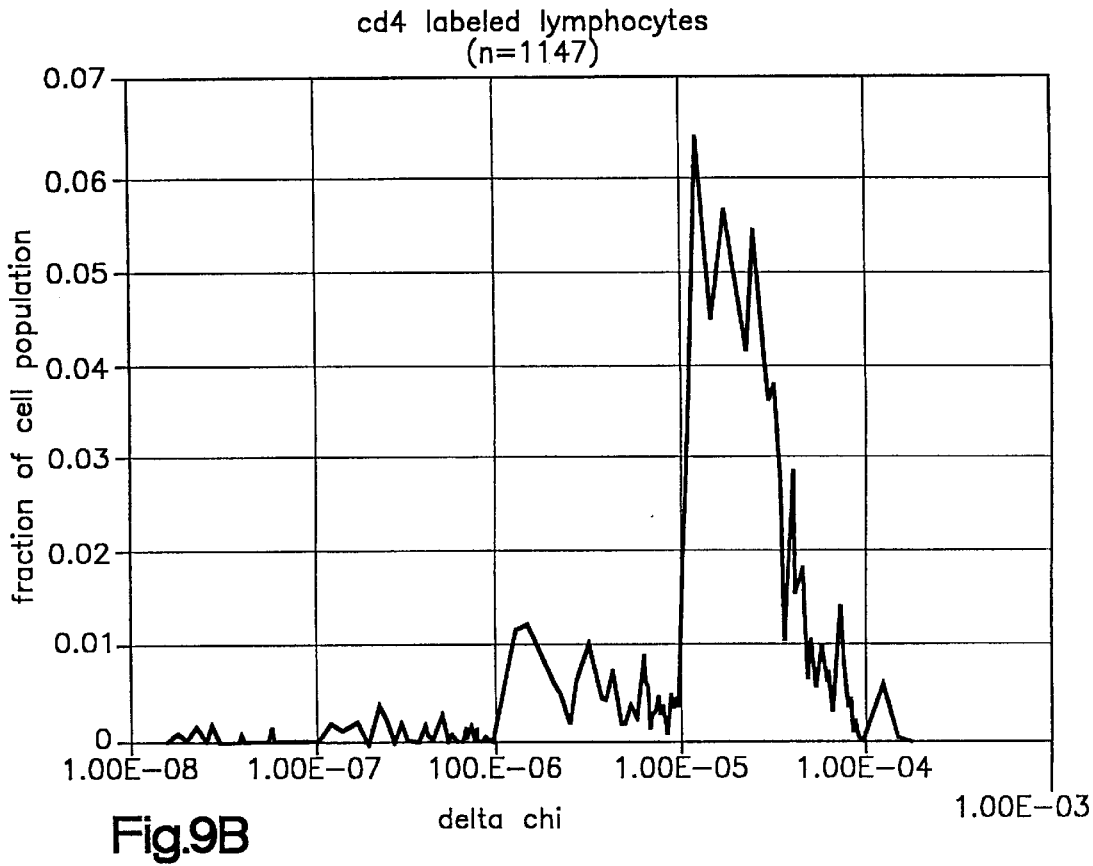
FIG. 9B is a graph showing the distribution of magnetic susceptibility of lymphocyte cells as determined by the present invention.

Specifically, as described above, the CTV logic is capable of determining the velocity of the cell $V_c = v_y$ and the cell diameter $D_c$. Additionally, since the force field device 102 of the present invention provides a substantially uniform magnetic force within a portion of the air gap, the $$\frac{dB^2}{dy}\Big|_{x=0}$$

term in the denominator of Equation (2) is represented by a constant. Given all the known variables, the magnetic susceptibility $\Delta\chi$ may be determined. Illustrated in FIG. 9B is a graph showing the distribution of magnetic susceptibility $\Delta_\chi$ of CD4 labeled lymphocytes which was generated by the present invention.

As described above, the present invention may alternatively employ cells which have been labeled with differential density labels such as, for example, high density (e.g., gold) and low density (e.g., polymeric particles) labels. Similar to paramagnetic labeling, density labeling of cells modifies the cell motion in response to the various force fields (e.g., gravitational field) which can be employed by the present invention. Alternatively, electrically-charged labels such as, for example, ions, can also be employed by the present invention. Similar to paramagnetic labeling and density labeling, electrically-charged labeling of cells also modifies the cell motion in response to the various force fields (e.g., electric field) which can be employed by the present invention. Moreover, combinations of paramagnetic, density, and electrically charged labeling may be employed to further class and sub-class particular cell populations of interest based on the presence or absence of particular labels. Once the motion of labeled cells has been analyzed to determine, for example, their velocity, other characteristics such as mass, acceleration, density, phagocytic capacity of negatively charged cells, etc., can be determined therefrom.

It should also be mentioned that a fluorescent label such as, for example, fluorochrome, may be additionally employed to class and sub-class cell populations of interest based on the presence or absence of one or more fluorescent labels. Light sources which are compatible with fluorescent labels include, for example, ultra-violet and visible light sources. The fluorescent labels preferably emit or transmit colors in the range of green, yellow, or red. Once labeled, the cells can be classed or sub-classed based on fluorescence.

While the present invention has been illustrated by the description of embodiments thereof, and while the embodiments have been described in considerable detail, it is not the intention of application to restrict or in any way limit the scope of the appended claims to such detail. Additional advantages and modifications will readily appear to those skilled in the art. For example, it is possible to stain cells with a fluorescent label and then use a laser for illumination. This would involve the use of specific instruments to detect the light emitted from the fluorescent labels. Moreover, the present invention can be utilized with any technique which allows for the classification of particles based the particles' behavior in the presence of a force field and/or electromagnetic energy. Therefore, the invention, in its broader aspects, is not limited to the specific details, the representative apparatus, and illustrative examples shown and described. Accordingly, departures may be made from such details without departing from the spirit or scope of the applicant's general inventive concept.

We claim:

1. A device for determining one or more particle physical characteristics, the device comprising:
   (a) a force field device for subjecting at least one particle to at least one force field, the force field device comprising:
      (1) a first force field producing assembly comprising:
         (i) a first force field producing device; and
         (ii) a first pole piece for concentrating the force field flux produced by the first force field producing device;
      (2) a second force field producing assembly comprising:
         (i) a second force field producing device; and
         (ii) a second pole piece for concentrating the force field flux produced by the second force field producing device;
      (3) the first and second pole pieces each comprising a flux concentrating portion having a curved end portion for producing a region of space having a substantially constant force field and wherein the flux concentrating portions are displaced substantially opposite each other with an inter-polar air gap therebetween and wherein the curved end portions comprise:
         (i) a first distal end having a substantially curved surface;
         (ii) a second distal end having a substantially curved surface;
         (iii) wherein the first and second distal ends are configured so as to be contiguous with each other; and
         (iv) wherein the substantially curved surface of the first distal end comprises a portion having a substantially constant radius and wherein the radius is in the range of approximately 3 mm; and
         (v) wherein the substantially curved surface of the second distal end comprises a portion which is substantially hyperbolic and wherein the hyperbolic portion is approximately defined as $y(x) = 9.544/x^2 - 12.719$, wherein x and y are Cartesian coordinates with the origin placed at the intersection of the plane of symmetry separating the pole pieces and a plane tangent to the radial portion of the distal ends of the pole pieces;
   (b) a substantially transparent flow channel positioned at least partially within the region of space having a substantially constant force magnitude and direction and for allowing the introduction of at least one particle; and
   (c) a computer system for gathering and analyzing data associated with the at least one particle.

2. The device of claim 1 wherein the first and second pole pieces further comprise substantially planar top and bottom surfaces, wherein the substantially planar bottom surface of the first pole piece is at least partly in physical contact with the first force field producing device and the substantially planar bottom surface of the second pole piece is at least partly in physical contact with the second force field producing device.

3. The device of claim 2 further comprising a force field control device for controlling the magnitude of the force field.

4. The device of claim 2 wherein the flux concentrating portion of the first force field producing assembly projects from the first force field producing device and the flux concentrating portion of the second force field producing assembly projects from the second force field producing device.

5. The device of claim 1 wherein the first and second force field producing devices are magnets.

6. The device of claim 1 wherein the first and second force field producing devices are electromagnets.

7. The device of claim 1 wherein the first and second force field producing devices are electric force field producing devices.

8. The device of claim 1 further comprising at least one utility space positioned near the region having a substantially constant force fielded.

9. The method of claim 1 wherein the particle is selected from a group consisting of: cells, cell organelles, platelets, inorganic, organic, biological, and polymeric particles which are optically visible.

10. A device for determining one or more particle physical characteristics, the device comprising:
   (a) a force field device for subjecting at least one particle to at least one force field, the force field device comprising:
      (1) a base;
      (2) first and second magnets coupled to the base for generating a magnetic flux;
      (3) first and second pole pieces coupled to the first and second magnets; the first and second pole pieces comprising a substantially planar shape having a magnetic flux concentrating portion; and
      (4) the first and second pole pieces further configured to provide an air gap and a utility space for accommodating data collection equipment, wherein the air gap at least partially forms a region of space having a substantially constant force magnitude and direction, and wherein the utility space is adjacent to the air gap;
   (b) a substantially transparent flow channel positioned at least partially within the region of space having a substantially constant force magnitude and direction and for allowing the introduction of at least one particle;
   (c) a computer system for gathering and analyzing data associated with the at least one particle; and
   (d) a camera located at least partially within the utility space.

11. The device of claim 10 further comprising a light source located at least partially within the utility space.

12. A device for determining one or more particle physical characteristics, the device comprising:
   (a) a force field device for subjecting at least one particle to at least one force field, the force field device comprising:
      (1) a base;
      (2) first and second magnets coupled to the base for generating a magnetic flux;
      (3) first and second pole pieces coupled to the first and second magnets; the first and second pole pieces comprising a substantially planar shape having a magnetic flux concentrating portion; and
      (4) the first and second pole pieces further configured to provide an air gap and a utility space for accommodating data collection equipment, wherein the air gap at least partially forms a region of space having a substantially constant force magnitude and direction, and wherein the utility space is adjacent to the air gap;
   (b) a substantially transparent flow channel positioned at least partially within the region of space having a substantially constant force magnitude and direction and for allowing the introduction of at least one particle;
   (c) a computer system for gathering and analyzing data associated with the at least one particle; and
   (d) a light source located at least partially within the utility space.

* * * * *